United States Patent [19]

Neumann

[11] Patent Number: 5,464,435
[45] Date of Patent: Nov. 7, 1995

[54] PARALLEL PROCESSORS IN IMPLANTABLE MEDICAL DEVICE

[75] Inventor: Robert A. Neumann, Blaine, Minn.

[73] Assignee: Medtronic, Inc., Minneapolis, Minn.

[21] Appl. No.: 191,674

[22] Filed: Feb. 3, 1994

[51] Int. Cl.⁶ ............................................ A61N 1/36
[52] U.S. Cl. ............................................. 607/9
[58] Field of Search ........................... 607/4–17

[56] References Cited

U.S. PATENT DOCUMENTS

| | | | |
|---|---|---|---|
| 4,250,884 | 2/1981 | Hartlaub et al. | 128/419 PT |
| 4,324,252 | 4/1982 | Rossing et al. | 128/419 PG |
| 4,374,382 | 2/1983 | Markowitz | 340/870.01 |
| 4,379,459 | 4/1983 | Stein | 128/419 |
| 4,407,288 | 10/1983 | Langer et al. | 128/419 PG |
| 4,476,868 | 10/1984 | Thompson | 128/419 PG |
| 4,485,813 | 12/1984 | Anderson | 128/675 |
| 4,523,595 | 6/1985 | Zibell | 128/419 D |
| 4,556,063 | 12/1985 | Thompson | 128/419 PT |
| 4,949,241 | 8/1990 | Iwasaki | 364/200 |
| 5,043,874 | 8/1991 | Gagliardo | 364/200 |
| 5,050,065 | 9/1991 | Dartois et al. | 364/200 |
| 5,055,999 | 10/1991 | Frank et al. | 364/200 |
| 5,056,000 | 10/1991 | Chang | 364/200 |
| 5,062,040 | 10/1991 | Bishop et al. | 364/200 |
| 5,062,046 | 10/1991 | Sumiyoshi | 364/200 |
| 5,065,759 | 11/1991 | Begemann | 128/419 |
| 5,084,836 | 1/1992 | Yamaguchi | 395/800 |
| 5,086,498 | 2/1992 | Tanaka | 395/200 |
| 5,099,414 | 3/1992 | Cole et al. | 395/200 |
| 5,103,393 | 4/1992 | Harris et al. | 395/650 |
| 5,109,356 | 4/1992 | Lawton | 364/726 |
| 5,121,502 | 6/1992 | Rau et al. | 395/8 |
| 5,135,004 | 8/1992 | Adams et al. | 128/696 |
| 5,148,812 | 9/1992 | Verrier et al. | 128/704 |
| 5,217,021 | 6/1993 | Steinhaus et al. | 128/702 |
| 5,240,009 | 8/1993 | Williams | 128/702 |

Primary Examiner—William E. Kamm
Assistant Examiner—Marianne Parker
Attorney, Agent, or Firm—Reed A. Duthler; Harold R. Patton

[57] ABSTRACT

A multi-function implantable medical device having a plurality of microprocessors therein. The device, which may be capable of functioning as a pacemaker, cardioverter, and defibrillator, is equipped with two or more processors, which may be configured in a master/slave, peer, or other type of relationship. In one embodiment, primary device functions to be performed continuously are allocated to a dedicated, master processor, while advanced functions that may be only periodically required, are allocated among one or more slave processors. In this way, processing in the device is not limited to the relatively short refractory periods as in prior devices.

6 Claims, 2 Drawing Sheets

PARALLEL PROCESSORS IN IMPLANTABLE MEDICAL DEVICE

FIELD OF THE INVENTION

This invention relates to the field of implantable medical devices, and more particularly relates to parallel processing in implantable medical devices.

BACKGROUND OF THE INVENTION

Many commercially available pacemakers employ internal microprocessors for control of various pacing functions and for mathematical calculations. An early digital pacemaker having a customized microprocessor was described, for example, in the above-referenced Hartlaub et al. patents. The inclusion of a general purpose microprocessor in an implanted devices was proposed in U.S. Pat. No. 4,407,288 to Langer et al., which patent is hereby incorporated by reference herein in its entirety.

As generally practiced, the use of a single microprocessor in an implantable device does not enable processing to be performed other than during the blanking intervals, as previously described. For a processor operating at 150,000 machine cycles per second, 18,000 machine cycles are available during a typical 120-mSec blanking period. Assuming an average of three-and-one-half machine cycles per instruction, only about 5100 instructions can be executed during a blanking interval. Certain of these instructions will be devoted to "housekeeping", memory tests, and other "overhead" tasks. Considerably more processing capability may be needed to implement more advanced features (e.g., waveform analysis, as previously described).

The number of instructions performed during the blanking interval can be increased by increasing microprocessor speed, but only at the cost of significant increases in current drain. Power consumption has always been an important consideration in the design of implantable medical devices, since it is desirable for an implantable device to be capable of operating for long periods of time before its battery is depleted. Power consumption becomes an even greater consideration in the context of implantable defibrillators and cardioverters, which as compared with pacemakers consume much larger amounts of power to deliver the larger stimulating pulses.

Relatively simple devices such as single-chamber pacemakers do not require all of the processing capability of a high speed, general purpose microprocessor, making the use of such a microprocessor inefficient for most tasks associated with timing and control of basic pacing functions. In the above-referenced Langer et al. '288 patent, there is proposed an arrangement wherein two microprocessors having differing levels of speed, processing capability, and power consumption, are incorporated into a single, multi-purpose implantable device. The microprocessors are chosen for controlling a particular type of operation to be implemented in the implantable device. In this way, a simpler, slower, and less power-consuming microprocessor is used to carry out long-term operations, while a more sophisticated processor of higher power and speed can be devoted to short-term processing-intensive operations. Also discussed in the Langer et al. '288 patent is the possibility that a single microprocessor in a multi-function implantable device could be activated in either of two modes, a slower, less-power consuming mode for long-term operations, and a faster, higher-power consuming mode for short-term, processing intensive operations.

SUMMARY OF THE INVENTION

The present invention relates to an implantable cardiac stimulator capable of performing in a multiplicity of operating modes to effect various different therapies as needed. Via a telemetry link, the various operating modes and the parameters for each mode can be non-invasively selected and programmed.

In accordance with one feature of the present invention, the multi-function cardiac stimulating device includes two or more parallel microprocessors. It is contemplated that one of the processors may be designated as a master processor, while others would be designated as slaves. Alternatively, the processors may be configured as peers. Each of the parallel processors is designed such that it has the ability to execute instructions utilizing internal random-access memory (RAM) and/or read-only memory (ROM), while tri-stating a common external address/data/control bus. Each parallel processor is preferably capable of accessing the others and/or a common RAM/ROM area by first gaining control of the common bus via a request to the master processor.

In accordance with the present invention, therefore, two or more programs could be executed simultaneously in the device, enhancing the device's ability to perform advanced functions and to perform multiple functions simultaneously.

In accordance with another feature of the present invention, a specified RAM area is used to store status information and data generated by the different programs currently being executed by the parallel processors. New data can be stored by one processor while diagnostics are performed on previously stored data, at the same time that the device is in communication with an external programmer.

In accordance with still another feature of the present invention, it is contemplated that the multiple processors in an implantable device could be operable in a redundant mode wherein if one parallel processor failed, another processor could assume control of at least the more basic and critical device functions. This is advantageously accomplished in accordance with the present invention by providing a subset or backup program for each processor to allow any of the parallel processors to provide at least a minimal level of operation.

In accordance with yet another feature of the present invention, however, it is contemplated that while a redundant mode of interoperability among the parallel processors is available, it is also possible that each processor can operate wholly independently of the others, thereby significantly increasing the potential functionality of the device. It is believed that the various functions and tasks to be performed by the device's circuitry can be advantageously apportioned among the various processors so that multiple functions can be performed concurrently.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein.

DETAILED DESCRIPTION OF A PREFERRED EMBODIMENT OF THE INVENTION

Figure 1:
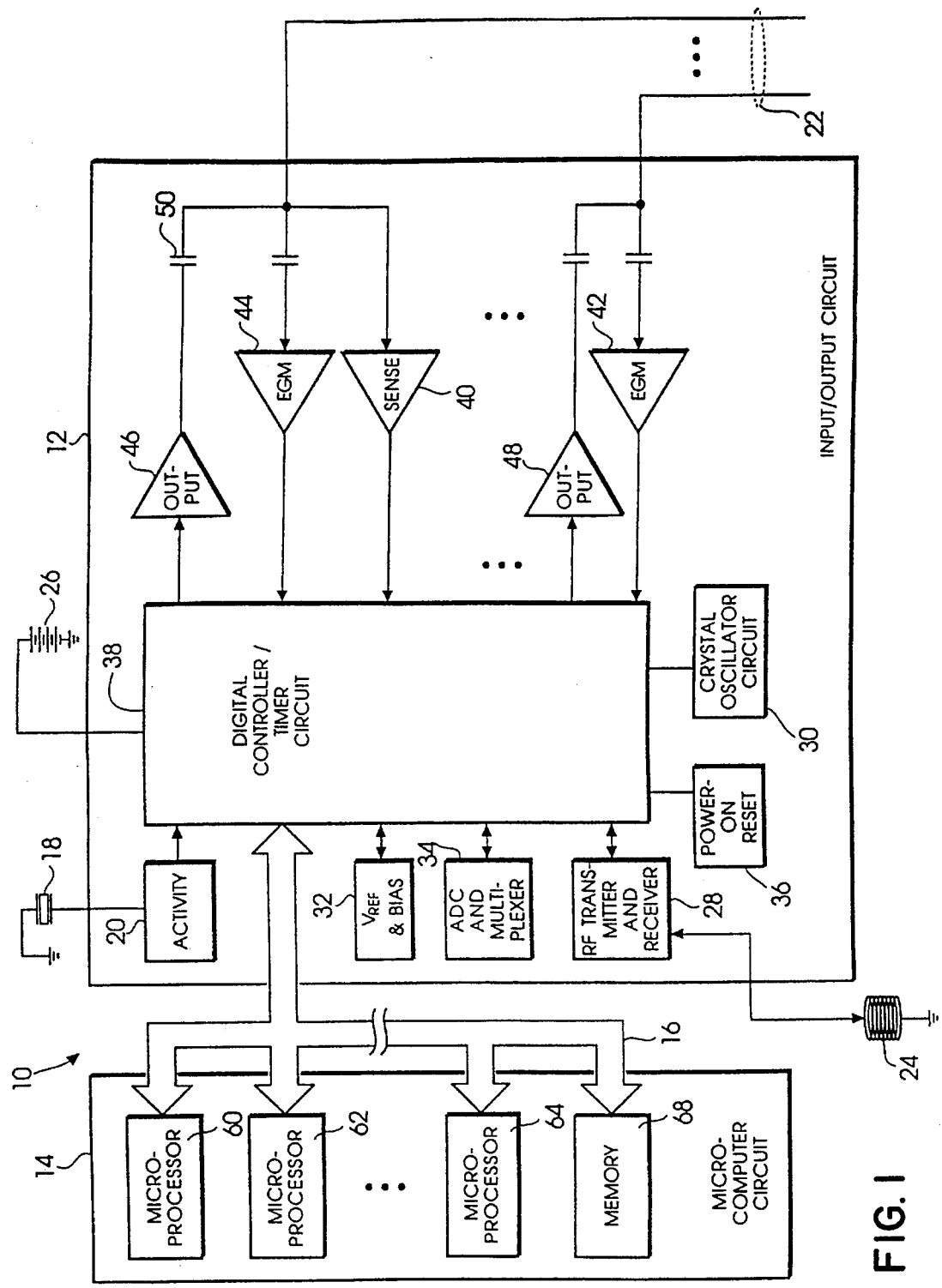
FIG. 1 is a block diagram of an implantable device in accordance with one embodiment of the present invention.

Referring to FIG. 1, there is provided a simplified block diagram illustrating the constituent components of an implantable medical device 10 in accordance with the presently disclosed embodiment of the invention is provided. In accordance with an important aspect of the present invention, implantable device 10 is microprocessor-based and includes multiple parallel processors. It is to be understood that the present invention may be advantageously utilized in the context of a multiple-function implantable device, for example, a device capable of performing pacing, cardioversion, and defibrillation, as well as various types of self-diagnostic functions and patient diagnostic functions.

The implantable device of FIG. 1 generally comprises two main components: an input/output circuit 12 and a microcomputer circuit 14. Microcomputer circuit 14, which shall be described herein in greater detail, is coupled to input/output circuit 12 by a multiple-conductor system bus 16 adapted to convey control, address, and data signals between the various components of implantable device 10.

In the illustrative embodiment shown in FIG. 1, implantable device 10 includes an activity sensor 18, which as previously noted may be, for example, a piezoelectric element bonded to the inside of the implantable device's hermetically-sealed outer canister, not shown in the FIGS. Such an activity sensor configuration is the subject of U.S. Pat. No. 4,485,813 to Anderson et al., which is hereby incorporated by reference in its entirety. Piezoelectric sensor 18 provides a sensor output which varies as a function of a measured parameter that relates to the metabolic requirements of the patient. This output is conveyed to activity circuitry 20 for processing.

Implantable device 10 of FIG. 1 is programmable by means of an external programming unit (not shown in the FIGS.). One such programmer suitable for the purposes of the present invention is the Medtronic Model 9710 programmer which has been commercially available for several years and is intended to be used with all Medtronic products. The programmer is a microprocessor based device which provides a series of encoded signals to implantable device 10 by means of a programming head which transmits radio-frequency (RF) encoded signals to device 10 according to the telemetry system laid out, for example, in U.S. Pat. No. 4,250,884 issued to Hartlaub et al which patent is hereby incorporated by reference in its entirety. It is to be understood, however, that the programming methodology disclosed in the Hartlaub et al. patent is identified herein for the purposes of illustration only, and that any programming methodology may be employed so long as the desired information is transmitted to the implantable device. It is believed that one of skill in the art would be able to choose from any of a number of available programming techniques to accomplish this task.

The programmer facilitates the selection by a physician of the desired parameter to be programmed and the entry of a particular setting for the desired parameter. For purposes of the present invention, the specifics of operation of the programmer are not believed to be important with the exception that whatever programmer is used must include means for selecting various operational parameters and settings therefor.

For example, for controlling the operation of device 10 in a pacing mode, various pacing parameters, including pacing mode, lower and upper rate limits, refractory intervals, escape intervals, sense amplifier sensitivity, pacing pulse amplitude and/or duration, rate response attack and decay, and the like, are selectable by means of the programmer. For controlling the operation of device 10 in a cardioverting mode, the parameters to be programmed include tachycardia onset detection criteria, cardioverting energy, and pulse amplitude, path, width, and pattern. Similarly, for controlling the operation of device 10 in a defibrillating mode, the programmable parameters include defibrillation onset criteria, and defibrillating pulse energy, amplitude, path, width, and pattern. Certain diagnostic and self-diagnostic operations may also require programmable control as well, as would be appreciated by those of ordinary skill in the art.

As shown in FIG. 1, a plurality of patient leads, designated collectively as 22, are coupled to device 10. It will be appreciated by those of ordinary skill in the art that leads 22 convey signals from electrodes (not shown) disposed at various sites within the patient, and convey stimulating pulses (e.g., pacing, cardioverting, or defibrillating pulses) to implanted electrodes. Some of the leads 22 may further convey signals from other types of implantable sensors, e.g., pressure sensors and the like, disposed in the patient.

In the presently disclosed embodiment, activity sensor 18 is bonded to the inside of the device's outer protective shield or can (not shown in FIG. 1), in accordance with common practice in the art. As shown in FIG. 1, the output from activity sensor 12 is coupled to activity circuitry 20 in input/output circuit 12.

Input/output circuit 12 contains the analog circuits for interface between device 10 and the patient's heart, activity sensor 18, and a telemetry antenna or coil 24. Input/output circuit 12 further contains circuits for the application of various types of stimulating pulses to the heart under control of the software-implemented algorithms in microcomputer circuit 14, to be hereinafter described in greater detail.

It will be understood that the electrical components represented in FIG. 1 are powered by an appropriate implantable battery power source 26, in accordance with common practice in the art. For the sake of clarity, the coupling of battery power to the various components of device 10 has not been shown in the FIGS. Antenna 24 is connected to input/output circuit 12 for purposes of uplink/downlink telemetry through RF transmitter and receiver unit 28. RF transmitter/receiver unit 28 may correspond to the programming logic employed in the above-referenced Hartlaub et al. patent and to the uplink telemetry circuitry described in U.S. Pat. Nos. 4,374,382 to Markowitz and in 4,556,063 to Thompson et al., both of which are incorporated herein by reference in their entireties. The particular programming and telemetry scheme chosen is not believed to be important for the purposes of the present invention so long as it provides for entry and storage of various programmable parameters, as previously discussed.

A crystal oscillator circuit 30, typically a 32,768-Hz crystal-controlled oscillator, provides main timing clock signals to digital controller/timer circuit 174. A $V_{REF}$ and Bias circuit 32 generates stable voltage reference and bias currents for the analog circuits of input/output circuit 12. An analog-to-digital converter (ADC) and multiplexer unit 34 digitizes analog signals (e.g., sensing signals or EGM signals) so that various digital values can be generated. For example, a patient's intracardiac electrogram can be digitized and transmitted in real time to an external display unit. Similarly, the voltage from battery 26 may be periodically measured, digitized, and provided in digital form either to microcomputer circuit 14 or to an external unit, for the purposes of monitoring battery depletion. A power-on-reset (POR) circuit 36 functions as a means to reset circuitry and related functions to a default condition upon detection of a low battery condition, which will occur upon initial device power-up or will transiently occur in the presence of electromagnetic interference, for example.

The operating commands for controlling the timing of operations by device 10 are coupled by bus 16 to a digital controller/timer circuit 38 wherein various digital timers and counters are provided for establishing and/or measuring various timing intervals and windows during operation of device 10.

With continued reference to FIG. 1, device 10 includes one or more sensing circuits which receive signals from leads 22. Two such sensing circuits, 40 and 42, are shown in FIG. 1, although it is to be understood that additional sensing circuits may be provided depending upon the types of electrodes and/or other sensors that may be coupled to device 10 via leads 22. Similarly, device 10 preferably includes an EGM amplifier 44 adapted to receive a patient's intracardiac electrogram. The EGM signal from amplifier 44 may be applied to ADC 34 for conversion to digital form. The digitized EGM may then be analyzed and/or stored in microcomputer circuit 14, or telemetered to an external device in real-time for display and/or analysis. Sense amplifier circuitry believed to be suitable for the purposes of the present invention is disclosed, for example, in U.S. Pat. No. 4,379,459 issued to Stein on Apr. 12, 1983, incorporated by reference herein in its entirety.

The device further includes one or more output pulse generator circuits. Two such circuits, 46 and 48, are shown in FIG. 1, although it is to be understood that other output circuits may be provided depending upon the level of functionality of device 10. For example, it is contemplated that separate output circuits may be provided for pacing and for cardioverting/defibrillating, since different types of stimulating pulses are required to perform these functions. In the embodiment of FIG. 1, output circuit 46 provides pacing stimuli to the patient's heart delivered from capacitor 50 in response to a pacing trigger signal developed by digital controller/timer circuit 38 each time the pacing escape interval times out, or an externally transmitted pacing command has been received, or in response to other stored commands as is well known in the pacing art. Output amplifiers in device 10 may correspond generally to the output amplifier disclosed in U.S. Pat. No. 4,476,868 issued to Thompson on Oct. 16, 1984 also incorporated herein by reference in its entirety.

While specific embodiments of input amplifiers 40 and 42 and output amplifiers 46 and 48 have been identified herein, this has been done for the purposes of illustration only. It is believed by the inventor that the specific embodiments of such circuits are not critical to the present invention so long as they provide means for generating the necessary stimulating pulses and provide digital controller/timer circuit 38 with sensing and/or sensor signals as required.

It is to be understood that the block diagram of FIG. 1 is greatly simplified, and that, as would be appreciated by those of ordinary skill in the art, there are a number of components conventionally included in implantable medical devices which are not represented in FIG. 1.

Figure 2:
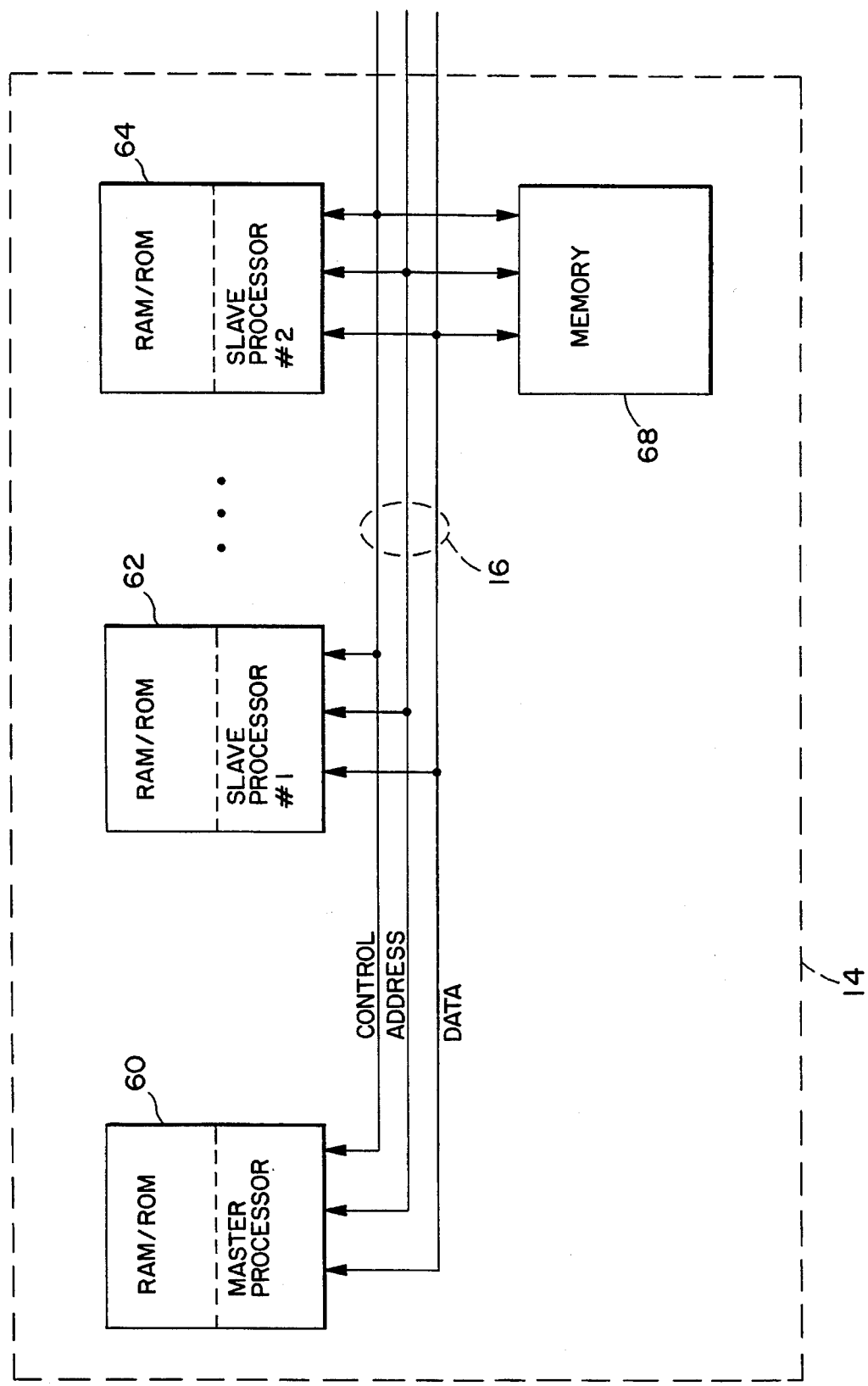
FIG. 2 is a block diagram of the microcomputer circuit in the implantable device of FIG. 1.

Referring now to FIG. 2, there is shown a block diagram of microcomputer circuit 14 in the device of FIG. 1 in accordance with the presently disclosed embodiment of the invention. It is to be understood that while three microprocessors, designated as 60, 62, and 64 in the FIGS., are shown in the presently disclosed embodiment of the invention, it is contemplated that any plurality of parallel processors can be employed in the practice of the present invention. Also, it is contemplated that microprocessors 60, 62, and 64 may be of the commercially-available, general-purpose type, numerous types of which are known. In the alternative, microprocessors 60, 62, and 64 may be custom-designed, limited-purpose processors, such as that disclosed in the above-referenced Hartlaub et al. patents.

As shown in FIG. 2, each of the microprocessors 60, 62, and 64 includes on-chip memory (RAM and/or ROM), as is commonly the case with commercially-available microprocessors. In addition to the on-chip memory of each microprocessor, microcomputer circuit 14 includes a separate memory unit 68, which preferably includes both general purpose RAM and non-volatile ROM storage.

In accordance with an important aspect of the present invention, it is contemplated that the many and various processing functions which must be performed by device 10 may be apportioned in several different ways among the plurality of microprocessors included in microcomputer circuit 14. It is believed that different allocations of processor capability offer different advantages in the context of an implantable medical device.

For example, by providing similar base level programming for each of the parallel processors, redundancy is achieved which makes the device highly fault-tolerant. If one processor were to fail, another one could assume control of the device. On the other hand, by providing different specialized programming for each parallel processor, multiple functions may be performed concurrently, thereby enhancing the device's functionality. It is believed that the choice of allocation of programming among the various processors can vary as desired in a given application of the present invention.

Certain factors must be addressed in providing parallel processing capability. As discussed above, one issue which must be addressed is the allocation of tasks to be performed among the various processors available. One option is to dedicate one processor to the primary device functions that must be constantly performed (e.g., waiting for detection of specified cardiac events and initiating responses thereto) and utilize the other processors as necessary to perform advanced device functions that may only periodically be required (e.g., rate response rate calculation, waveform analysis, self-diagnostic functions, advanced telemetry functions, patient diagnostic functions, and the like). U.S. Pat. No. 5,103,393 to Harris et al. entitled "Method of Dynamically Allocating Processors in a Massively Parallel Processing System" addresses the issue of allocating processors to tasks on a dynamic basis. Although the Harris '393 patent describes a massively parallel processing system, it is believed that the concepts disclosed therein could be advantageously adapted to the present invention. The Harris '393 patent is hereby incorporated by reference herein in its entirety.

It is also contemplated that in the event that one parallel processor fails, control of device 10 may be transferred to one of the remaining processors. This is especially important in the context of an implantable medical device, which preferably includes safeguards to maintain the device in an operating state at all times. U.S. Pat. No. 5,062,046 to Sumiyoshi et al. entitled "Multiple Processor System Having a Correspondence Table for Transferring Processing Control Between Instruction Processors" describes an arrangement for transferring processing control from one processor to another. It is believed that the Sumiyoshi '046 invention could be advantageously practiced in conjunction with the present invention. The Sumiyoshi '046 patent is hereby incorporated by reference herein in its entirety.

In some embodiments of the invention, one of the microprocessors, for example, microprocessor 60, is designated as a "master" processor, while the remaining processors, 62 and 64, are designated as "slave" processors. Designation of each processor as master or slave may be accomplished, for example, as a mask option during the manufacture of the integrated circuits.

Master/slave arrangements are described in U.S. Pat. No. 5,056,000 to Chang, entitled "Synchronized Parallel Processing With Shared Memory" and in U.S. Pat. No. 4,949,241 to Iwasaki et al. entitled "Microcomputer System Including a Master Processor and a Slave Processor Synchronized by Three Control Lines". The Change '000 and Iwasaki '241 patents are hereby incorporated by reference herein in their entireties.

If a master/slave arrangement of multiple processors is employed, primary operations of implanted device 10 could be performed by the master processor, while secondary operations could be assigned to a slave processor, which can perform such secondary operations without the blanking period time restrictions to which the master is subjected. For example, a slave processor may be employed to perform morphologic analysis of a patient's intracardiac electrogram analysis, so that various different types of cardiac events can be accurately detected and distinguished from one another. For example, the slave processor may be dedicated to S-T segment storage and analysis as in U.S. Pat. No. 5,135,004, issued to Adams et al., Ventricular waveform morphology storage and analysis as disclosed in U.S. Pat. Nos. 4,523,595, issued to Zibell and 5,240,009, issued to Williams and U.S. Pat. No. 5,217,021, issued to Steinhaus et al. or T-wave alternates analysis as disclosed in U.S. Pat. No. 5,148,812 issued to Verrier et al., all of which are incorporated herein by reference in their entireties.

Such morphologic analysis can be a numerically intensive task which could easily monopolize the processing capability of a single processor. In the implantable device 10 in accordance with the present invention, on the other hand, the "number-crunching" required for morphologic analysis could be performed by a slave processor. The program steps corresponding to the morphologic analysis algorithm could be stored in a slave processors's on-chip memory, so that the slave processor operates independently from the master.

In U.S. Pat. No. 5,065,759, issued to Begemann et al. and incorporated herein by reference in its entirety, them is described a relatively computationally intensive techniques for modulating rate-response parameters in activity and respiration sensing pacemakers. The processing required to determine pacing rates in the Begemann et al. device could similarly be allocated to a slave processor, leaving the master processor free to perform the primary pacemaker functions.

The use of parallel processors to perform numerically intensive signal processing functions, is discussed in U.S. Pat. No. 5,084,836 to Yamaguchi entitled "Parallel Signal Processing System", and U.S. Pat. No. 5,109,356 to Lawton entitled "Apparatus for Computation of Discrete Fourier Transform Using Array Parallel Processor". The Yamaguchi '836 and Lawton '356 patents are hereby incorporated by reference in their entireties.

With a master/slave arrangement of parallel processors, power consumption can be reduced by causing the slave processors to enter a standby or "sleep" mode when they are not being called upon to perform a task. When the master processor determines that there is a task that can be allocated to a slave, it can activate the slave and direct it (for example, by providing a subroutine address on the address bus) to begin executing the desired code. The master processor could even be responsible for first loading the desired subroutine from common memory unit 68 into the slave processor's local, on-chip memory, as necessary.

In addition to a master/slave arrangement, it is also contemplated that parallel processors 60, 62, and 64 could be configured, either in the design phase or on a dynamic basis, to operate in a concurrent fashion wherein each processor independently executes the same or wholly independent algorithms. As an alternative, each processor could be configured to operate in a redundant mode, wherein if one of the parallel processors failed, a remaining processor could assume control of device 10, executing a subset or backup code providing a minimal level of operation. As a further alternative, the configuration of parallel processors in device 10 may be dynamically reconfigurable. A reconfigurable parallel processing system is described, for example, in U.S. Pat. No. 5,050,065 to Dartois et al. entitled "Reconfigurable Multiprocessor Machine for Signal Processing". The Dartois '065 patent is hereby incorporated by reference herein in its entirety.

Regardless of whether a master/slave, peer, or other type of relationship among the parallel processors in device 10 is employed, it will be appreciated by those of ordinary skill in the computer art that provision must be made for enabling multiple processors to access not only their own respective local (i.e., on-chip) memories, but also the common system memory unit 68. It is also important for the parallel processors in device 10 to be capable of communicating among themselves. In U.S. Pat. No. 5,121,502 to Rau et al. entitled "System for Selectively Communicating Instructions From Memory Locations Simultaneously or From the Same Memory Locations Sequentially to Plurality of Processors", U.S. Pat. No. 5,043,874 to Gagliardo et al. entitled "Memory Configuration for Use With Means for Interfacing A System Control Unit for a Multi-Processor System With the System Main Memory", and U.S. Pat. No. 5,055,999 to Frank et al. entitled "Multiprocessor Digital Data Processing System", there are discussed various configurations for allowing multiple processor access to share system memory. The Rau et al. '502, Gagliardo et al. '874, and Frank et al. '999 patents are hereby incorporated by reference herein in their entirety, as it is believed that the concepts discussed therein may be advantageously applied in the practice of the present invention.

Regarding interprocessor communications, one suitable arrangement is described in U.S. Pat. No. 5,086,498 to Tanaka et al. entitled "Parallel Computer with Asynchronous Communication Facility". The Tanaka et al. reference, which is hereby incorporated by reference in its entirety, is believed to be particularly complementary to the present invention, since implantable medical devices are often required to be responsive to asynchronous events, such as detected cardiac events and the like. U.S. Pat. No. 5,062,040 to Bishop et al. entitled "Handling of Notification of Asynchronous Events by User and Stub Processes of a Distributed Process Executing on a Plurality of Processors of a Multi-Processor System", and U.S. Pat. No. 5,099,414 to Cole et al. entitled "Interrupt Handling in a Multi-Processor Data Processing System" also discuss the handling of asynchronous events in a multi-processor context. The Bishop et al. '040 patent and Cole et al. '414 patents are also hereby incorporated by reference herein in their entireties.

The volatility of conventional digital memory is also of particular concern in the context of an implantable medical device, whether or not the device is microprocessor-based. In U.S. Pat. No. 4,324,252 to Rossing et al. entitled "Memory Control Circuitry For Implantable Medical Devices", there is described circuitry for setting volatile semiconductor memory to a known condition if the battery voltage drops below acceptable levels. The Rossing et al. '252 patent is hereby incorporated by reference herein in its entirety.

Considerable time is often required to test an implantable medical device during the manufacturing process. This testing time is naturally longer for more complex devices. In one manufacturing technique, each integrated circuit in the system is thoroughly tested before it is incorporated into the system. After all of the integrated circuits have been assembled, it becomes more difficult to thoroughly test each device. In order to facilitate the testing process, it is contemplated that self-test or self-diagnostic programs could be utilized within each of the parallel processors to test other components of the system throughout the manufacturing phase and even after manufacturing is complete.

In the specific context of an implantable pacemaker or an implantable pacemaker/cardioverter/defibrillator, a particularly preferable interrelationship of master and slave processors is accomplished by providing a priority list of processor based functions, stored in memory 68, along with programming associated with a selected set of microprocessor functions, which may be transferred to the RAM memories associated with each individual processor. The priority list in this specific embodiment would be employed by the master processor to allocate slave processor functions, in circumstances in which one or more slave processors was disabled. For example, in a system employing a master processor for controlling basic cardiac pacing functions as typically employed in current microprocessor based devices, separate slave processors may be employed for waveform analysis and for rate response function calculations, respectively. In the event of a failure of the slave processor being employed to perform rate response calculations, which are deemed higher on the priority list than morphology analysis and storage, the slave processor previously employed to perform morphology analysis could be switched over to perform the rate response calculation function, by transfer of software from memory 68. Alternatively, each of the slave processors may include memory covering both of the slave processor functions, so that the master processor can simply specify which of the stored programs each of the slave processors is intended to perform.

Particularly in the context of an implantable pacemaker or implantable pacemaker/cardioverter/defibrillator, it is also advantageous if each of the slave processors includes programming corresponding to a minimum, base level device functionality. For example, in a device configured as a dual chamber rate responsive pacemaker, the master processor may include programming for controlling basic dual chamber pacing functions including software for deriving values of the various timing intervals (pacing, sensing, refractory) employed by the device during the dual chamber pacing mode, with the slave processor employed to calculate rate response values in response to sensor outputs. The slave processor may also include basic software for controlling the operation of the device in a more limited mode, for example simple VVI pacing, which would be activated in the event of a failure of the master processor to function appropriately. This redundancy would provide an additional level safety in the context of an implantable devices.

In the specific context of an implantable pacemaker or pacemaker/cardioverter/defibrillator, it is particularly advantageous for the master processor and the slave processors to have different activation or wake up criteria. The master processor, for example, would typically be awakened on each sensed heart depolarization and on each delivered pacing pulse, whereas the slave processor might be activated only in response to detection of a defined arrhythmia condition for waveform morphology analysis, or might be activated only in response to time out of defined intervals with regard to activation of rate response calculations.

From the foregoing detailed description of a specific embodiment of the invention, it should be apparent that an implantable device having a plurality of parallel processors has been disclosed. The disclosed system can be advantageously configured such that each parallel processor operates wholly independently from the others, and that some processors may be temporarily deactivated when not needed, in order to reduce power consumption. It is believed that the disclosed system offers significant advantages, in that processing capability, self-diagnostic capability, and reliability of the device is enhanced.

Although a specific embodiment of the invention has been described herein in some detail, this has been done for the purpose of illustration only, and is not intended to limit the scope of the present invention to the particular embodiment described. It is contemplated that numerous design options may be exercised, as discussed above, and that various alterations, substitutions, and modifications to the disclosed device can be made without departing from the spirit and scope of the present invention as defined in the appended claims, which follow.

What is claimed is:

1. A multiple-function implantable medical device, comprising:

an independently programmable master processor;

at least one independently programmable slave processor;

an address, data, and control signal bus interconnecting said master and slave processors;

a main memory unit, coupled to said bus;

a plurality of local memory units, each one of said local memory units associated with and accessible by one of said master processor and said at least one slave processor, wherein at least two of said local memory units store identical instructions; and a therapy delivery means, coupled to said address, data and control signal bus, said delivery means responsive to control signals on said bus, for delivering a plurality of therapies;

wherein each of said local memory units stores instructions for causing a processor associated therewith to issue, on said address, data, and control signal bus, control signals corresponding to a specific one of said plurality of therapies.

2. A multiple-function implantable medical device, comprising:

multiple independently programmable processors;

an address, data, and control signal bus interconnecting said processors;

a main memory unit, coupled to said bus;

a plurality of local memory units, each one of said local memory units associated with and accessible by a different one said processors, wherein at least two of said local memory units store identical instructions; and a therapy delivery means, coupled to said address, data and control signal bus, said delivery means responsive to control signals on said bus, for operating in a plurality of therapeutic modes;

wherein each of said local memory units stores instructions for causing a processor associated therewith to issue, on said address, data, and control signal bus, control signals corresponding to a specific one of said plurality of therapeutic modes.

3. A multiple-function implantable medical device, comprising:

an independently programmable master processor;

at least one independently programmable slave processor;

an address, data, and control signal bus interconnecting said master and slave processors;

a main memory unit, coupled to said bus;

a plurality of local memory units, each one of said local memory units associated with and accessible by one of said master processor and said at least one slave processor; and a therapy delivery means, coupled to said address, data and control signal bus, said delivery means responsive to control signals on said bus, for delivering a plurality of therapies;

wherein each of said local memory units stores instructions for causing a processor associated therewith to issue, on said address, data, and control signal bus, control signals corresponding to a specific one of said plurality of therapies;

said device further comprising means for storing a listing of functions to be performed by said processors and means for reallocating said functions among said processors, according to said listing, in response to failure of one of said processors.

4. A multiple-function implantable medical device, comprising:

multiple independently programmable processors;

an address, data, and control signal bus interconnecting said processors;

a main memory unit, coupled to said bus;

a plurality of local memory units, each one of said local memory units associated with and accessible by a different one said processors; and a therapy delivery means, coupled to said address, data and control signal bus, said delivery means responsive to control signals on said bus, for operating in a plurality of therapeutic modes;

wherein each of said local memory units stores instructions for causing a processor associated therewith to issue, on said address, data, and control signal bus, control signals corresponding to a specific one of said plurality of therapeutic modes;

said device further comprising means for storing a listing of functions to be performed by said processors and means for reallocating said functions among said processors, according to said listing, in response to failure of one of said processors.

5. A multiple-function implantable medical device, comprising:

an independently programmable master processor;

at least one independently programmable slave processor;

an address, data, and control signal bus interconnecting said master and slave processors;

a main memory unit, coupled to said bus;

a plurality of local memory units, each one of said local memory units associated with and accessible by one of said master processor and said at least one slave processor; and a therapy delivery means, coupled to said address, data and control signal bus, said delivery means responsive to control signals on said bus, for delivering a plurality of therapies;

wherein each of said local memory units stores instructions for causing a processor associated therewith to issue, on said address, data, and control signal bus, control signals corresponding to a specific one of said plurality of therapies;

said device further comprising means responsive to failure of one of said processors for altering the instructions executed by another of said processors.

6. A multiple-function implantable medical device, comprising:

multiple independently programmable processors;

an address, data, and control signal bus interconnecting said processors;

a main memory unit, coupled to said bus;

a plurality of local memory units, each one of said local memory units associated with and accessible by a different one said processors; and a therapy delivery means, coupled to said address, data and control signal bus, said delivery means responsive to control signals on said bus, for operating in a plurality of therapeutic modes;

wherein each of said local memory units stores instructions for causing a processor associated therewith to issue, on said address, data, and control signal bus, control signals corresponding to a specific one of said plurality of therapeutic modes;

said device further comprising means responsive to failure of one of said processors for altering the instructions executed by another of said processors.

* * * * *